(12) United States Patent
Tao

(10) Patent No.: US 11,808,729 B2
(45) Date of Patent: Nov. 7, 2023

(54) INTERFACE CIRCUIT FOR AN ELECTROCHEMICAL SENSOR

(71) Applicant: EM MICROELECTRONIC-MARIN SA, Marin (CH)

(72) Inventor: Yonghong Tao, Singapore (SG)

(73) Assignee: EM MICROELECTRONIC-MARIN SA, Marin (CH)

( * ) Notice: Subject to any disclaimer, the term of this patent is extended or adjusted under 35 U.S.C. 154(b) by 552 days.

(21) Appl. No.: 16/858,987

(22) Filed: Apr. 27, 2020

(65) Prior Publication Data

US 2020/0363368 A1    Nov. 19, 2020

(30) Foreign Application Priority Data

May 16, 2019   (EP) ..................................... 19174802

(51) Int. Cl.
  *G01N 27/327*      (2006.01)
  *G01N 27/404*      (2006.01)
  (Continued)

(52) U.S. Cl.
  CPC ..... *G01N 27/4045* (2013.01); *A61B 5/14532* (2013.01); *G01N 27/3273* (2013.01); *G01N 33/53* (2013.01)

(58) Field of Classification Search
  CPC ........... G01N 27/3273; G01N 27/4045; G01N 27/4065; G01N 33/05; A61B 5/14532
  See application file for complete search history.

(56) References Cited

U.S. PATENT DOCUMENTS 5,880,638 A * 3/1999 Schaffer ................ H03F 3/3001
                                                         330/261
9,933,387 B1 * 4/2018 McCanna .......... G01N 27/3273
(Continued)

FOREIGN PATENT DOCUMENTS

CN           105445329 A  *  3/2016  ............. G01N 27/00

OTHER PUBLICATIONS

Thipnet et al., "Portable Voltammetric Device for Detecting Heavy Metal Contamination," American Journal of Engineering Research (AJER), 2016, vol. 5, issue-11, pp. 285-296 (Year: 2016).*
(Continued)

*Primary Examiner* — Alexander S Noguerola
(74) *Attorney, Agent, or Firm* — Sughrue Mion, PLLC

(57) ABSTRACT

A sensor interface circuit (5) for an amperometric electrochemical sensor (3). The circuit includes: a current-to-voltage converter (9, Rf) connected to a first terminal (WRK) of the sensor (3) for converting an electric current through the sensor (3) to a voltage at an output terminal (10) of the current-to-voltage converter (9, Rf); a first amplifier (7) connected between a second terminal (REF) and a third terminal (CNTR) of the sensor (3) for maintaining a substantially fixed voltage difference between the first and second terminals (WRK, REF) of the sensor (3); a power supply (11) for powering the voltage converter (9, Rf) and for powering a first portion (31) of the first amplifier (7); and a negative voltage converter (17) configured to power a second portion of the first amplifier (7) through its low-side supply terminal (41), while a high-side supply terminal (39) of the second portion of the first amplifier (7) is configured to be connected to the power supply (11).

14 Claims, 2 Drawing Sheets

(51) Int. Cl.
*A61B 5/145* (2006.01)
*G01N 33/53* (2006.01)

(56) References Cited

U.S. PATENT DOCUMENTS

2005/0110574 A1  5/2005  Richard et al.
2008/0174372 A1  7/2008  Tucker et al.
2011/0127163 A1  6/2011  Brooks

OTHER PUBLICATIONS

EPO computer-generated English language translation of the Description section of Fu-jie Liu CN 105445329 A, downloaded Sep. 13, 2022, patent published Mar. 30, 2016 (Year: 2016).*
Ashok Bindra, "Generating Negative Output from Positive Input Voltage," Digi-Key web article, published Oct. 16, 2012 ; downloaded from https://www.digikey.com/en/articles/generating-negative-output-from-positive-input-voltage (Year: 2012).*
Jim Karki, "Application Report—Understanding Operational Amplifier Specifications," Texas Instruments White Paper: SLOAO11, Apr. 1998 (Year: 1998).*
Renesas Data Sheet for the ICL7660 Cmos Voltage converter, FN3072, Rev. 7.00, Oct. 5, 2010 (Year: 2010).*
Phakhamon Thipnet Dissertation, "Portable Voltammetric Device for Detecting Heavy Metal Contamination," Faculty of Science, Burapha University, Dec. 2016 (Year: 2016).*
Scott D. Adams et al., "MiniStat: Development and Evaluation of a Mini-Potentiostat for Electrochemical Measurements", IEEE Access, pp. 31903-31912, Mar. 25, 2019, vol. 7.
European Search Report for EP 19 17 4802 dated Nov. 8, 2019.

* cited by examiner

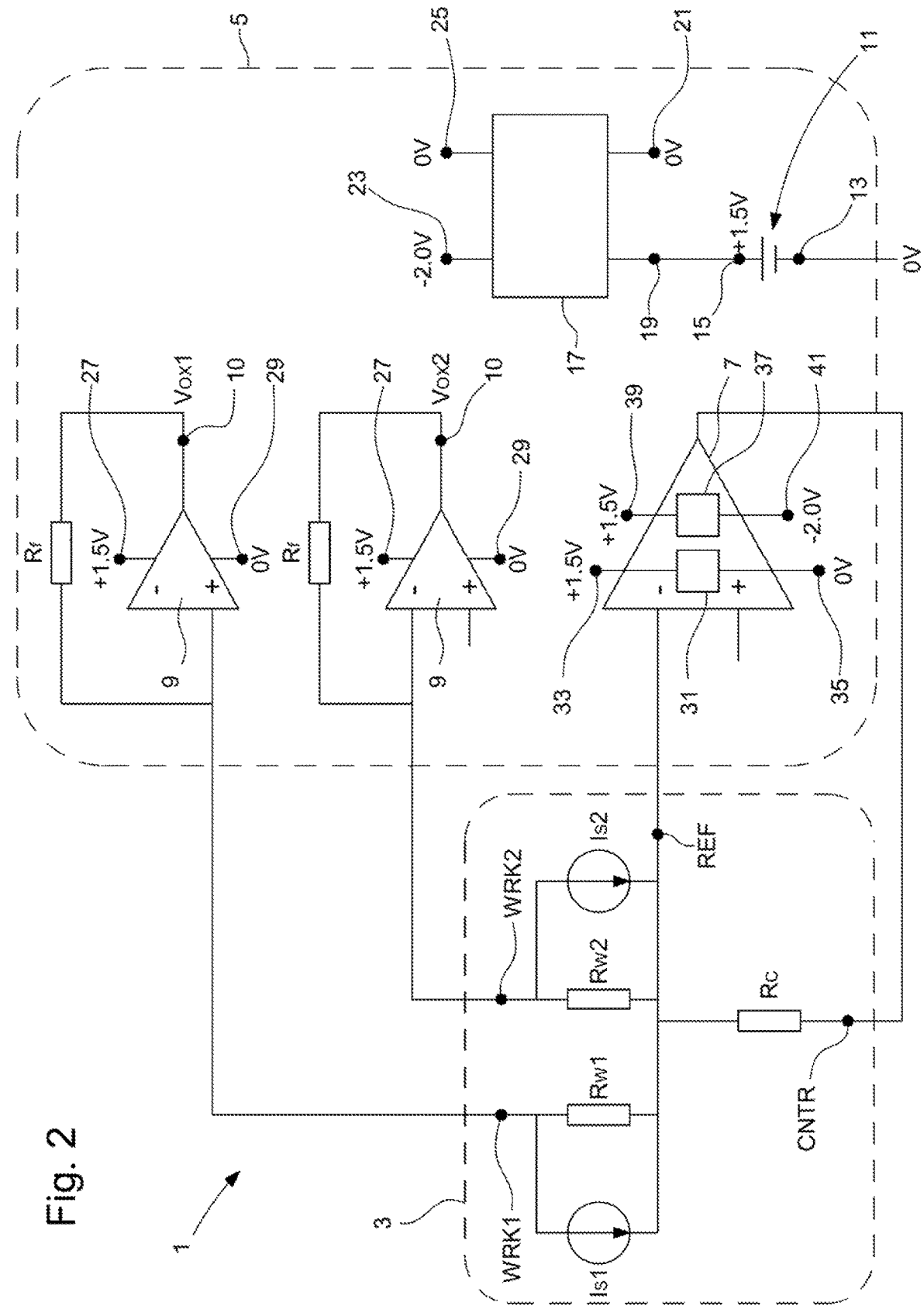

INTERFACE CIRCUIT FOR AN ELECTROCHEMICAL SENSOR

TECHNICAL FIELD

The present invention relates to a sensor interface circuit for an electrochemical sensor, such as a glucose sensor. The invention also relates to a sensor system comprising the sensor interface circuit and a sensor.

CROSS-REFERENCE TO RELATED APPLICATIONS

This application claims priority to European Patent Application No. 19174802.9, filed on May 16, 2019, the entire contents of which are incorporated herein by reference.

BACKGROUND OF THE INVENTION

Electrochemical sensors are widely used in the areas of environmental monitoring, industry automation and clinical analyses. Such sensors can be classified into different types based on the sensing mechanism: potentiometric, amperometric and conductometric. In amperometric sensors, a current is generated which is proportional to the concentration of the chemical under test. One example application of such amperometric sensors is portable glucose sensing for continuous diabetes monitoring. These kinds of portable continuous glucose monitoring systems are powered up by a tiny battery with limited capacity. In order to achieve desired life time, low power consumption is very critical for such a sensing system. However, existing electrochemical sensor systems have often the drawback that they have a rather high power consumption, which leads to a limited life time.

SUMMARY OF THE INVENTION

An object of the present invention is to overcome at least some of the above shortcomings of the existing electrochemical sensors or their interface circuit.

According to a first aspect of the invention, there is provided an amperometric sensor interface circuit as recited in claim 1.

The proposed solution has the advantage that the power consumption of the interface circuit can be reduced compared to existing amperometric sensor interface circuits. Thus, the proposed interface circuit is a low power interface circuit that may be used for measuring the current from a glucose sensor for instance. Furthermore, by using the proposed interface circuit both the system size and the manufacturing costs can be reduced.

According to a second aspect of the invention, there is provided a sensor system comprising the above interface circuit and further comprising an electrochemical sensor.

Other aspects of the invention are recited in the dependent claims attached hereto.

BRIEF DESCRIPTION OF THE DRAWINGS

Other features and advantages of the invention will become apparent from the following description of a non-limiting example embodiment, with reference to the appended drawings, in which:

FIG. 2 is a simplified circuit diagram illustrating an alternative sensor system design according to a second embodiment of the present invention.

DETAILED DESCRIPTION OF THE INVENTION

Figure 1:
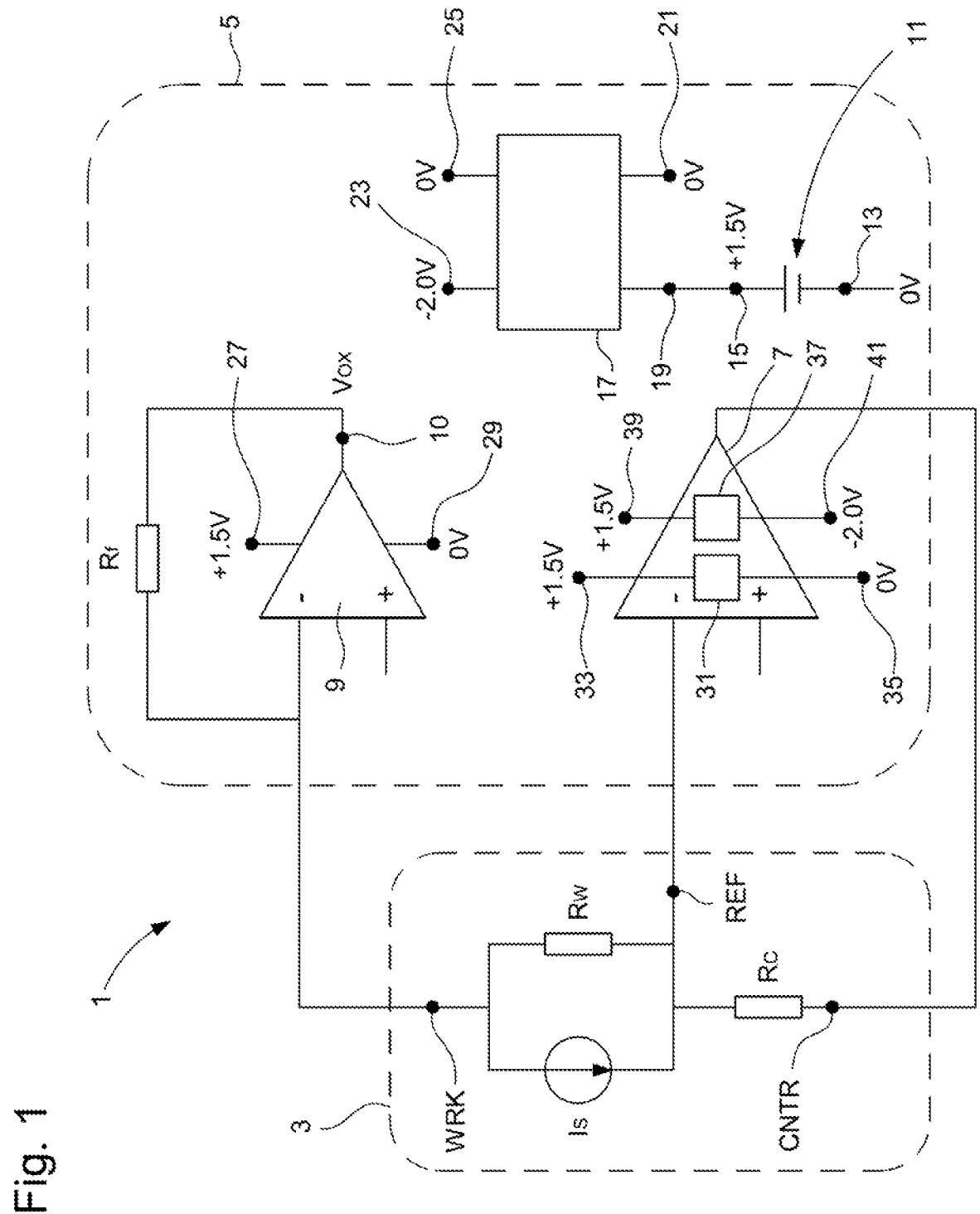
FIG. 1 is a simplified circuit diagram illustrating a sensor system according to a first embodiment of the present invention.

An embodiment of the present invention will now be described in detail with reference to the attached figures. The invention will be described in the context of an amperometric glucose sensor circuit or system. However, the teachings of the invention are not limited to this environment or application. For example, the teachings of the present invention may be also used for other types of amperometric electrochemical sensor systems. Identical or corresponding functional and structural elements which appear in different drawings are assigned the same reference numerals. As utilised herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z." Furthermore, the term "comprise" is used herein as an open-ended term. This means that the object encompasses all the elements listed, but may also include additional, unnamed elements. Thus, the word "comprise" is interpreted by the broader meaning "include", "contain" or "comprehend".

The circuit diagram of FIG. 1 schematically illustrates an amperometric electrochemical sensor circuit or system 1 according to a first embodiment. An amperometric electrochemical sensor 3 can be presented by an electrical model shown in FIG. 1. It has three electrodes, nodes or terminals: a first electrode or working electrode or terminal (referred to as a WRK terminal in FIG. 1), a second electrode or reference electrode or terminal (referred to as a REF terminal in FIG. 1) and a third electrode or a counter electrode or terminal (referred to as a CNTR terminal in FIG. 1). A current source Is is connected between the WRK terminal and the REF terminal. The mode of operation of the electrochemical sensor involves the production of an electrical signal by reaction with the analyte of interest. In this example, glucose reacts with the sensor to produce a current Is, the value of which depends on the sensed glucose concentration. The current Is flows from the WRK terminal to the CNTR terminal. The current can then be measured by a sensor interface circuit or system 5, which may also be called a sensor measurement circuit or system. In this example, the sensor requires a fixed voltage to be applied between the WRK terminal and the REF terminal, which in this example is nominally 40 mV for the adopted sensor. A first impedance or resistor Rw, which is arranged in parallel with the current source Is, represents a small leakage current that will exist at 0% glucose concentration. A second impedance or resistor Rc exists between the REF terminal and the CNTR terminal. The resulting voltage difference between the WRK and CNTR terminals would vary depending on the glucose level, with the maximum up to 2 V for the adopted sensor. The sensor interface circuit 5 should satisfy all these requirements. In addition, the leakage current through the REF terminal should ideally be limited, for example, up to 10 pA for the adopted sensor.

Although the sensor modelled in FIG. 1 will be used for the following explanations, the teachings of the present invention can be extended to other variants of sensors with similar but not necessarily identical configurations. For example, the specifications of the sensors from different manufacturers could be different. For example, the required fixed voltage between the WRK and REF terminal can be 100 mV while the required output difference between the WRK and CNTR terminals can be up to 2.5 V. It is to be noted that in the present description, all numerical values are given merely for illustration purposes but they by no means are intended to limit the scope of the present invention. It is further to be noted that for ideal amplifiers used in the present application, the desired output range is up to 2 V. The required supply voltage for the amplifiers should be greater than the desired output range voltage level. The difference between the supply voltage (in particular the positive supply voltage) and the desired output range is called headroom in the present description.

As shown in FIG. 1, the sensor interface circuit 5 is connected to the sensor 3 for measuring the current flowing in the sensor. A first amplifier 7, and more specifically a loop controlling amplifier, which is a first operational amplifier, is connected between the REF and CNTR terminals of the sensor so that its inverting input (with − sign in FIG. 1) is connected to the REF terminal, while the output of the first amplifier 7 is connected to the CNTR terminal. The REF terminal of the sensor is thus advantageously connected to a high impedance node, which in this example is the inverting input of the first amplifier 7. The non-inverting input (with + sign in FIG. 1) is in this example kept at a fixed electric potential, and more specifically in this example at 0.50 V, in order to maintain a fixed voltage difference between the WRK and REF terminals. In this manner a correct current value at different glucose levels can be obtained. It is to be noted that there is substantially no voltage difference between the inverting input and the non-inverting inputs of the first amplifier 7, if zero offset errors are assumed for the amplifiers shown in the circuit of FIG. 1. In the present example, the output of the first amplifier 7 can vary from −1.50 V to 0.50 V according to the sensor output current. In such configuration, the maximum allowed voltage difference between the WRK and CNTR terminals is up to 2.0 V.

The sensor interface circuit 5 also comprises a current-to-voltage converter or a trans-impedance amplifier formed in this case by a second amplifier 9, which is a second operational amplifier, and a third (large valued) resistor or a feedback resistor Rf arranged in a feedback loop of the second amplifier. The first and second operational amplifiers may be implemented for instance by using complementary metal-oxide-semiconductor (CMOS) transistors. The trans-impedance amplifier 9 converts the sensor signal (current) Is into an output voltage Vox at the output terminal 10 of the second amplifier. The voltage Vox may then be signal conditioned (for example by low pass filters) and digitised by an analogue-to-digital converter (ADC). In order to leave some headroom for the Vox signal, the non-inverting input of the second amplifier is biased at a fixed electric potential, and in this example at 0.54 V (as stated previously, all the numbers are merely for illustration purposes). Thus, in view of the above numerical values, a fixed voltage difference of 40 mV (0.54 V−0.50 V=40 mV) is maintained between the WRK and REF terminals. Here again, there is substantially no voltage difference between the inverting input and the non-inverting input of the second amplifier 9. It is to be noted that it would instead be possible to construct the current-to-voltage converter with discrete components using a field effect transistor for the gain element. The current-to-voltage converter together with the first amplifier can be considered to form an analogue front-end for the sensor.

The sensor interface circuit 5 further comprises a power source or supply 11 and more specifically a direct current (DC) power supply, which in this example is a battery, and more specifically a +1.5 V battery. The battery has a first, negative or low-side output terminal 13, and a second, positive or high-side output terminal 15. In this example, the first output terminal is at a voltage level of 0 V, while the second output terminal is at a voltage level of 1.5 V.

The sensor interface circuit 5 also comprises a negative voltage converter 17 or a positive-to-negative voltage converter, which is provided between the battery and its load, which in this example is the first amplifier 7. The negative voltage converter 17 may thus be considered to be in a series configuration with the battery 11. The purpose of the negative voltage converter is to perform supply-voltage conversions from a positive voltage level to a negative voltage level. In other words, the negative voltage converter is configured to generate a negative voltage output from a positive input. It may also be configured to produce a stable output voltage in an application that has a widely varying input. Thus, the negative voltage converter 17 can be considered to be a voltage manipulating block placed between the battery 11 and its load, in order to feed the energy to the load with a desired polarity and voltage level. There are many ways to implement the negative voltage converter, one example being based on CMOS switched-capacitors.

An input terminal 19 of the negative voltage converter 17 is connected, in this example directly, to the second output terminal 15 of the battery. A first reference voltage terminal 21 of the negative voltage converter is at a fixed voltage level, which in this example equals 0 V. The negative voltage converter has an output terminal 23, which in this example is at a voltage level of −2.0 V, and a second reference voltage terminal 25, which is at a fixed voltage level, which in this example equals 0 V. The first and second reference voltage terminals are thus in this example grounded. The first amplifier 7, the trans-impedance amplifier 9 and the negative voltage converter 17 may all be integrated into one integrated circuit or semiconductor chip. It is to be noted that the negative voltage converter could have more than one input terminal and/or more than one output terminal such that one of them (having a negative voltage level) would be selectively connected at a time to the first amplifier 7. It is also to be noted that one single output terminal can provide current to multiple loads at the same time, through the same output terminal.

The proposed design thus uses only one battery for low cost and small system size. The second amplifier 9 is powered by the battery directly or through a voltage regulator, such as a low-drop-out (LDO) voltage regulator, for higher supply noise immunity. More specifically, a first, positive or high-side supply terminal 27 of the second amplifier 9 is connected to the second output terminal 15 of the battery 11, while a second, negative or low-side supply terminal 29 of the second amplifier 9 is connected to the first output terminal of the battery 11. The battery is thus arranged to supply electric power to the second amplifier 9 and thus to the trans-impedance amplifier. It is to be noted that the role of the negative voltage converter is similar to that of the LDO (voltage regulator), which is also placed between the battery and its load. The difference between the negative voltage converter and the LDO is substantially merely on the voltage polarity.

A first part or portion 31 of the first amplifier 7 is also powered by the battery 11 either directly or through a voltage regulator, such as an LDO voltage regulator, in order to support the required output range. More specifically, a first, positive or high-side supply terminal 33 of the first portion 31 of the first amplifier 7 is connected to the second output terminal 15 of the battery 11, while a second, negative or low-side supply terminal 35 of the first portion 31 of the first amplifier 7 is connected to the first output terminal 13 of the battery 11. A second portion 37, which in this example is different from the first portion, of the first amplifier is powered either directly or through a voltage regulator by both the battery 11 and the negative voltage converter 17. More specifically, in this example, a first, positive or high-side supply terminal 39 of the second portion 37 of the first amplifier 7 is connected to the second output terminal 15 of the battery 11, while a second, negative or low-side supply terminal 41 of the second portion 37 of the first amplifier 7 is connected to the negative output terminal 23 of the negative voltage converter 17.

Thus, advantageously, the on-chip negative voltage converter 17 is used to generate a given negative voltage, which in this example substantially equals −2.0 V, which is the low-side supply of some parts (the second portion) inside the first amplifier 7. Depending on the first amplifier topology, optimal partitioning could be found to achieve lowest total power consumption. The total power consumption can then be calculated in the current example as P=1.5 V×(supply current of the second amplifier 9)+1.5 V×(supply current for the first portion of the first amplifier 7)+3.5 V×(supply current for the second portion of the first amplifier 7)/(efficiency of the negative voltage converter). The supply current is the current flowing from a respective high-side supply terminal to a respective low-side supply terminal. The first portion may be e.g. the input stage of the first amplifier 7, while the second portion may be e.g. the output stage of the first amplifier 7. The input stage takes both the inverting input and non-inverting input of the first amplifier and converts their difference into an internal signal processed by the amplifier. The output stage converts the processed internal signal to an output signal.

Compared with sensor interface circuits that comprise two batteries e.g. in a series configuration, or one battery connected to a positive voltage converter, the present single battery configuration combined with the negative voltage converter 17 according to the present invention consumes less power, has a smaller circuit size and has a lower cost. Furthermore, in addition, according to the present invention, a signal conditioning and/or ADC circuits could also operate under the battery supply voltage. Accordingly, the overall power consumption at a system level is much lower than that in the conventional designs. More specifically, at a system level, the proposed solution may have a power consumption, which is only about one third of a power consumption of a traditional design having two batteries or one battery combined with a positive voltage converter. It is to be also noted that the proposed design can easily satisfy all the requirements imposed by the sensor design. By using the above example numerical values, the WRK terminal can be forced to 0.54 V and the REF terminal is forced to 0.50 V, leading to a substantially fixed voltage difference of 40 mV between these two terminals. The CNTR terminal could go down to as low as −1.5 V, such that the voltage difference from the WRK terminal to the CNTR terminal could be up to 2.0 V.

The circuit diagram of FIG. 2 schematically illustrates a sensor system 1 according to the second embodiment of the present invention. The sensor 3 according to this embodiment has two working electrodes or terminals for two-channel measurements, namely a first working terminal WRK1 and a second working terminal WRK2. The current in the sensor is modelled by a first current source Is1 and a second current source Is2. Furthermore, instead of the resistor Rw as in the configuration of FIG. 1, the sensor 3 comprises resistors Rw1 and Rw2 as shown in FIG. 2. The sensor interface circuit 5 according to the second embodiment comprises two trans-impedance amplifiers 9 as opposed to only one as in the first embodiment. More specifically, a first trans-impedance amplifier providing a first output voltage Vox1 is connected to the first working terminal WRK1, while a second trans-impedance amplifier providing a second output voltage Vox2 is connected to the second working terminal WRK2. The first and second trans-impedance amplifiers are in this example substantially identical and are thus powered by the battery 11.

The proposed sensor system may be used for instance as a portable or non-portable meter for measuring the amount of glucose (sugar) in a user's (or someone else's) blood. Using a blood glucose meter can help the user better manage diabetes by tracking any fluctuations in the user's blood glucose level. Depending on the actual sensor design, the measurements may be carried out invasively or non-invasively. However, it is to be noted that present invention is by no means limited to glucose measurements.

It was descried above a sensor interface circuit and a sensor system comprising the sensor interface circuit and additionally also a sensor for measuring or sensing a desired parameter. The invention equally relates to a method of operating the sensor interface circuit and the sensor system by supplying power to the first and second amplifiers as described above by the battery (power supply) and the negative voltage converter.

While the invention has been illustrated and described in detail in the drawings and foregoing description, such illustration and description are to be considered illustrative or exemplary and not restrictive, the invention being not limited to the disclosed embodiment. Other embodiments and variants are understood, and can be achieved by those skilled in the art when carrying out the claimed invention, based on a study of the drawings, the disclosure and the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

What is claimed is:

1. A sensor interface circuit for an amperometric electrochemical sensor, the sensor interface circuit comprising:
   a current-to-voltage converter connected to a first terminal of the amperometric electrochemical sensor for converting an electric current through the amperometric electrochemical sensor to a voltage at an output terminal of the current-to-voltage converter,
   a first amplifier connected between a second terminal and a third terminal of the amperometric electrochemical sensor for maintaining a substantially fixed voltage difference between the first and second terminals of the amperometric electrochemical sensor, the first amplifier comprising:
      a first portion that includes a first low-side supply terminal and a first high-side supply terminal;
      a second portion, different from the first portion, that includes a second low-side supply terminal and a second high-side supply terminal;

a first amplifier non-inverting input connected to the first portion; and
a first amplifier inverting input connected to the first portion;
a power supply for powering the current-to-voltage converter and for powering the first portion of the first amplifier, and
a negative voltage converter configured to power the second portion of the first amplifier through the second low-side supply terminal of the second portion, while the second high-side supply terminal of the second portion of the first amplifier is directly or indirectly connected to the power supply,
wherein a high-side output terminal of the power supply is directly or indirectly connected to the first high-side supply terminal of the first portion of the first amplifier for powering the first portion of the first amplifier,
a low-side output terminal of the power supply is connected to the first low-side supply terminal of the first portion of the first amplifier,
the first portion comprises input stage components of the first amplifier, while the second portion comprises output stage components of the first amplifier,
the first low-side supply terminal of the first portion is configured to be at zero volts based on being connected to the low-side output terminal of the power supply, and
the second low-side supply terminal of the second portion is configured to be at a negative voltage based on being connected to the negative voltage converter.

2. The sensor interface circuit according to claim 1, wherein an output terminal of the negative voltage converter is directly or indirectly connected to the second low-side supply terminal of the second portion of the first amplifier for powering the second portion of the first amplifier.

3. The sensor interface circuit according to claim 1, wherein the high-side output terminal of the power supply is directly or indirectly connected to a high-side supply terminal of the current-to-voltage converter for powering the current-to-voltage converter, while the low-side output terminal of the power supply is connected to a low-side supply terminal of the current-to-voltage converter.

4. The sensor interface circuit according to claim 1, wherein the high-side output terminal of the power supply is directly or indirectly connected to the second high-side supply terminal of the second portion of the first amplifier for powering the second portion of the first amplifier.

5. The sensor interface circuit according to claim 1, wherein the power supply is a battery.

6. The sensor interface circuit according to claim 1, wherein the negative voltage converter is placed between the first amplifier and the power supply such that an input terminal of the negative voltage converter is connected to the high-side output terminal of the power supply.

7. The sensor interface circuit according to claim 1, wherein the current-to-voltage converter comprises a transimpedance amplifier comprising a second amplifier and a feedback resistor arranged in a feedback loop of the second amplifier.

8. The sensor interface circuit according to claim 1, wherein the negative voltage converter comprises one or more reference voltage terminals at a fixed electric potential.

9. The sensor interface circuit according to claim 1, wherein the first amplifier, the current-to-voltage converter and the negative voltage converter are arranged on a single integrated circuit chip.

10. The sensor interface circuit according to claim 1, wherein a voltage regulator is arranged between the first amplifier and the power supply and/or the negative voltage converter, and/or between the current-to-voltage converter and the power supply.

11. The sensor interface circuit according to claim 1, wherein the current-to-voltage converter comprises a second amplifier comprising a second amplifier non-inverting input, and wherein the first amplifier non-inverting input is configured to be kept at a first fixed electric potential level, while the second amplifier non-inverting input is configured to be kept at a second, different fixed electric potential level.

12. A sensor system comprising the sensor interface circuit according to claim 1 and an amperometric electrochemical sensor.

13. A sensor system according to claim 12, wherein the amperometric electrochemical sensor is a glucose sensor.

14. The sensor interface circuit according to claim 1, wherein
the high-side output terminal of the power supply is directly or indirectly connected to the second high-side supply terminal of the second portion of the first amplifier for powering the second portion of the first amplifier,
the first high-side supply terminal of the first portion is configured to be at a positive voltage based on being connected to the high-side output terminal of the power supply, and
the second high-side supply terminal of the second portion is configured to be at the positive voltage based on being connected to the high-side output terminal of the power supply.

* * * * *